(12) United States Patent
Bedin et al.

(10) Patent No.: US 9,778,260 B2
(45) Date of Patent: Oct. 3, 2017

(54) PROCESS FOR THE DETECTION AND EARLY SEROTYPING OF THE DENGUE VIRUS

(75) Inventors: Frederic Bedin, Lyons (FR); Sandrine Busseret, Lyons (FR); Marine Steidel, Fellering (FR)

(73) Assignee: BIOMERIEUX, Marcy l'Etoile (FR)

( * ) Notice: Subject to any disclaimer, the term of this patent is extended or adjusted under 35 U.S.C. 154(b) by 439 days.

(21) Appl. No.: 14/113,631

(22) PCT Filed: Apr. 26, 2012

(86) PCT No.: PCT/FR2012/050926
§ 371 (c)(1),
(2), (4) Date: Oct. 24, 2013

(87) PCT Pub. No.: WO2012/153031
PCT Pub. Date: Nov. 15, 2012

(65) Prior Publication Data
US 2014/0051067 A1    Feb. 20, 2014

(30) Foreign Application Priority Data

May 6, 2011 (FR) ..................... 11 53916

(51) Int. Cl.
| | | |
|---|---|---|
| C07K 16/10 | (2006.01) |
| C12Q 1/70 | (2006.01) |
| C07K 14/005 | (2006.01) |
| C12N 7/00 | (2006.01) |
| A61K 39/00 | (2006.01) |
| G01N 33/569 | (2006.01) |
| G01N 33/68 | (2006.01) |

(52) U.S. Cl.
CPC ... G01N 33/56983 (2013.01); G01N 33/6851 (2013.01); *G01N 2333/185* (2013.01); *G01N 2800/56* (2013.01)

(58) Field of Classification Search
CPC .............. A61K 2300/00; A61K 39/395; A61K 39/39558; A61K 2039/505
See application file for complete search history.

(56) References Cited

FOREIGN PATENT DOCUMENTS

| FR | 2 794 864 A1 | 12/2000 |
|---|---|---|
| FR | 2794864 | * 12/2000 |
| WO | WO 2010/043973 A1 | 4/2010 |
| WO | WO2010043973 | * 4/2010 |

OTHER PUBLICATIONS

Halstead; "Dengue;" Lancet; Nov. 10, 2007; vol. 370; pp. 1644-1652.
Leong et al; "The pathology of dengue hemorrhagic fever;" Seminars in Diagnostic Pathology; 2007; vol. 24; pp. 227-236.
Clyde et al; "Recent Advances in Deciphering Viral and Host Determinants of Dengue Virus Replication and Pathogenesis;" Journal of Virology; 2006; vol. 80; No. 23; pp. 11418-11431.
Smith et al; "Synthesis of Proteins and Glycoproteins in Dengue Type 2 Virus-infected Vero and *Aedes albopictus* Cells;" J. gen. Virol.; 1985; vol. 66; pp. 559-571.
Avirutnan et al; "Vascular Leakage in Severe Dengue Virus Infections: A Potential Role for the Nonstructural Viral Protein NSI and Complement;" The Journal of Infectious Diseases; 2006; vol. 193; pp. 1078-1088.
Flamand et al; "Dengue Virus Type 1 Nonstructural Glycoprotein NSI is Secreted from Mammalian Cells as a Soluble Hexamer in a Glyocosylation-Dependent Fashion;" Journal of Virology; Jul. 1999; vol. 73; No. 7; pp. 6104-6110.
Kuwata et al; "Direct Detection and Quantitative Determination of Bovine Lactoferricin and Lactoferrin Fragments in Human Gastric Contents by Affinity Mass Spectrometry;" *Advances in Lactoferrin Research*; 1998; pp. 23-32.
Ashok et al; "Protective efficacy of a plasmid DNA encoding Japanese encephalitis virus envelope protein fused to tissue plasminogen activator signal sequences: studies in a murine intracerebral virus challenge model;" Vaccine; 2002; vol. 20; pp. 1563-1570.
Köhler et al; "Derivation of specific antibody-producing tissue culture and tumor lines by cell fusion;" Eur. J. Immunol.; 1976; vol. 6; pp. 511-519.
Frank et al; "Simultaneous Multiple Peptide Synthesis Under Continuous Flow Conditions on Cellulose Paper Discs as Segmental Solid Supports;" Tetrahedron; 1988; vol. 44; No. 19; pp. 6031-6040.
Vaughan et al; "Meta-analysis of All Immune Epitope Data in the *Flavivirus* Genus: Inventory of Current Immune Epitope Data Status in the Context of Virus Immunity and Immunopathology;" Viral Immunology; 2010; vol. 23; No. 3; pp. 259-284.
Jul. 5, 2012 Search Report issued in International Patent Application No. PCT/FR2012/050926 (with translation).
Translation of Jul. 5, 2012 Written Opinion issued in International Patent Application No. PCT/FR2012/050926.

\* cited by examiner

*Primary Examiner* — Janet L Andres
*Assistant Examiner* — Barry A Chestnut
(74) *Attorney, Agent, or Firm* — Oliff PLC

(57) ABSTRACT

Disclosed is a process for in vitro detection of an infection by a dengue virus in an individual, including the following steps: contacting a blood sample from the individual with a ligand specific to the NS1 protein of said dengue virus, to capture NS1 protein if it is present in the blood sample, said ligand being immobilized on a solid support; detecting the presence of NS1 protein via a mass spectrometry reading; and if NS1 protein is detected, concluding that the individual has been infected by dengue virus.

7 Claims, 3 Drawing Sheets

PROCESS FOR THE DETECTION AND EARLY SEROTYPING OF THE DENGUE VIRUS

Figure 1:
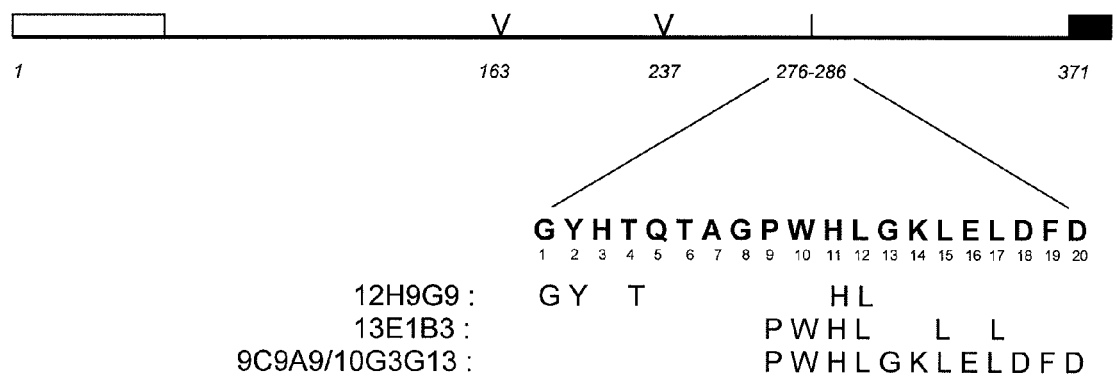

The object of the present invention is a process for the detection and early serotyping of the dengue virus.

Over the past 30 years, dengue, a viral disease transmitted by urban hematophagous mosquitoes of the genus *Aedes*, has spread around the world in an alarming manner. It is at present a real public health problem for more than one hundred countries situated in the subtropical zone, especially in the Pacific West, South America and South-East Asia zones. The emergence of the disease is due in large part to the population explosion and chaotic urbanisation. Climate anomalies too play a considerable role. As such, dengue could emerge in Western regions of the globe hitherto spared by the virus. Indeed, *Aedes albopictus*, one of the vectors of the disease, has recently been found in northern Italy and southern France. Lately, home-grown cases of dengue have been reported in southern France. It is estimated that nearly 3 billion people are exposed to the risks of dengue. There are nearly one million hospitalisations recorded every year, and deaths number in the thousands. Children are the chief victims of the disease.

Dengue virus is a positive-polarity single-stranded RNA enveloped virus of the Flaviviridae family. The virus genome (11,000 nucleotides) encodes for a polyprotein of approximately 3400 amino acids, which undergoes co- and post-translational cleavage resulting in structural proteins (C, prM, E) and non-structural proteins (NS1, NS2A, NS2B, NS3, NS4A, NS4B, NS5). There are 4 viral serotypes (DV1 to DV4), which can coexist in endemic zones. There is approximately 70% sequence homology between the different serotypes. Infection by a given serotype confers long-term immunity for this serotype. Cross-protection only lasts for a few months: so reinfection is possible with a different serotype. The most common clinical manifestation (dengue fever, or DF) is a febrile state lasting a few days, accompanied in particular by severe headaches, lower-back, muscle and joint pains, which regress spontaneously without specific treatment. However, complications can sometimes be encountered which lead to dengue haemorrhagic fever (or DHF). In this case, we can note a transient increase in vascular permeability, and plasma leakage responsible for thrombopenia and coagulopathy. In the most severe cases, plasma leakage may cause a fatal hypovolemic shock (DSS, Dengue Shock Syndrome) if the patient is not treated quickly. Liver and neurological injuries, rare but fatal, are also associated with the severity of the disease. The mortality rate, which may vary depending on the epidemics, may reach 5% of declared cases of DHF. This rate may rise to 20% without hospital care or suitable treatments.

90% of cases of DHF occur upon secondary infection by a heterologous serotype, and 10% upon a primary infection, usually in infants aged 6 months to 1 year. There are several factors affecting the severity of the infection, such as the host factors, the virus serotype and genotype, the order of succession of infecting viruses, the quality and quantity of cross-reacting antibodies and the CD4/CD8 response. However, the exact causes of the appearance of DHF are not always known with certainty. A first hypothesis has it that the selective forces exerted on the virus lead to the selection of a "super virus". Studies have shown a correlation between the viral load and the severity of the disease. Studies have also implicated viral proteins E and NS1 in pathogenicity. The sequence of infecting serotypes and the interval between each infection are also important clinical determinants. Thus a secondary infection by serotypes 1 and 2 is often associated with a high frequency of DHF. Until now, no specific determinants of virulence had been discovered with certainty. A secondary infection with a different serotype is significantly associated with the severity of the disease. This is the basis of the second hypothesis, the hypothesis that the infection is facilitated by low-affinity anti-dengue antibodies, which it has never been possible to confirm in vivo in the absence of an animal model. It is based on the presence of low-affinity neutralising antibodies which facilitate in vitro infection of macrophages via their immunoglobulin Fc receptor. The presence of immune complexes also promotes the activation of the complement. The activation and excessive proliferation of the memory T lymphocytes CD4 and CD8+ supposedly causes increased production of cytokines and cellular mediators. The concomitance of these various factors is supposedly responsible for the pathogenesis. While the determination of the key role of lymphocyte activation and mediator secretion in physiopathology is fairly well accepted, it is very difficult to show a clear correlation with the appearance of DHF.

Genetic factors probably play a role since several studies have shown the either protective or pathogenic role of certain HLA class 1 alleles. However, the results are fairly contradictory, and vary according to the source of the specimens.

At present, there are no commercially available vaccines against dengue virus, and the only treatments available are symptomatic treatments. In this context, it is important to be able to monitor the epidemics and predict severe cases to ensure appropriate hospital care[1, 2, 3].

Diagnosis of dengue is based on the detection of viral elements or specific antibodies. Among the conventional virology techniques, isolation of the virus by cell infection and immunofluorescence examination remains one of the benchmark techniques. However, it is technically highly onerous to employ.

Molecular methods (RT-PCR . . . ) enable virus detection and serotyping. Among the serological methods, MAC-ELISA (Immunoglobulin M Antibody Capture ELISA), which measures specific IgMs, is used to detect primary infections. However, they need to be associated with detection of specific IgGs in order to distinguish between primary and secondary infections. Yet the antibodies appear only 4-5 days after the beginning of the symptoms, and furthermore two samples need to be taken in order to detect seroconversion.

The NS1 protein was characterised in 1985 by G. W Smith[4]. It is a glycoprotein highly conserved in flaviviruses. Although its function has not been fully explained, it would appear to be involved in particular in virus replication and in pathogenicity. It is synthesised in monomer form. Its maturation is associated with dimerisation. The mature protein is transported to the plasma membrane and then excreted into the extracellular medium, where it is encountered in the form of dimers and multimers, mainly pentamers and hexamers[6].

Searching for NS1 protein in blood specimens from patients makes it possible to determine a recent infection, but does not make it possible to distinguish between primary and secondary dengue, which is an important factor, since DHF is mainly associated with a second infection by a different serotype.

ELISA methods have been developed to detect the presence of the NS1 viral protein and diagnose a dengue upon the appearance of fever. In these methods, use of mixtures of monoclonal antibodies and/or of polyclonal antibodies selected for their affinity to NS1 protein, enables early detection, during the clinical phase of the infection.

The problem with these ELISA methods is that they require use of at least two antibodies, a capture antibody and a detection antibody directed against different epitopes of the protein, which entails constraints in the selection of raw materials and technical constraints in performing the test. Furthermore, these methods do not make it possible to distinguish the various serotypes, even though it has been established that a secondary infection by serotypes 1 and 2, for example, is often associated with a high frequency of DHF.

Hence it is important to have a simpler detection method making it possible to detect NS1 protein early in a sample early, to establish the diagnosis of an infection, whether it is primary or secondary, and also to distinguish the various serotypes, particularly serotypes associated with a high frequency of DHF.

The present invention addresses the issues discussed above by means of a process making it possible both to detect early and specifically the NS1 protein in a biological sample, and to distinguish the different serotypes.

Thus, the object of the present invention in particular relates to a process of in vitro detection of a dengue viral infection in an individual, which comprises the following steps:

contacting a blood sample from the individual with a ligand specific to the NS1 protein of said dengue virus, to capture NS1 protein if it is present in the blood sample, said ligand being immobilised on a solid support, detecting the presence of NS1 protein via a mass spectrometry reading, and if NS1 protein is detected, concluding that the individual has been infected by dengue virus.

Mass spectrometry is a method which uses a mass spectrometer to detect ions in gaseous phase. A mass spectrometer comprises a source for ionising in gaseous state the molecules to be analysed, e.g. a laser, and an analyser to determine the nature of the mass using various physical principles. By way of example, as physical principles, mention may be made of TOF (Time Of Flight), ion trap, ion cyclotron resonance, quadripole filter, magnetic sector, and electrostatic sector.

MALDI-TOF mass spectrometers are mass spectrometers coupling a matrix-assisted laser ionisation source (MALDI: *Matrix-Assisted laser Desorption/Ionisation*) with a time of flight (TOF) analyser. Historically, time of flight analysers, which require a pulsed ionising source, were only coupled with MALDI sources. At present, MALDI sources may be coupled to other types of analyser (for example an FT-ICR analyser), and the time of flight analyser to other sources (for example an electrospray source in an ESI-QTOF instrument).

SELDI-TOF MS (*Surface Enhanced Laser Desorption/Ionisation Time Of Flight Mass Spectrometry*) is an approach developed by Hutchens et al.[7]. In this technique, proteins are retained on chromatographic surfaces mounted on well strips, and are then ionised by means of the MALDI technique and detected by TOF MS (Time Of Flight Mass Spectrometry). The chromatographic surfaces are designed to select the proteins present in a complex mixture, on criteria of hydrophobicity, charge, affinity, etc. The molecular mass of the proteins retained by the chromatographic surfaces can be measured by TOF MS.

Thus, according to a particular embodiment of the invention, the blood sample from the individual is contacted with a ligand specific to the NS1 protein of said dengue virus to capture NS1 protein if it is present in the blood sample, said ligand being immobilised on a solid support, the support undergoes a mass spectrometry reading to detect the presence of NS1 protein, and if NS1 protein is detected, it is concluded that the individual has been infected by dengue virus.

Besides the fact that the mass spectrometry detection method, particularly MALDI-TOF and SELDI-TOF, makes it possible to differentiate the different serotypes, it also has the advantage of only requiring the use of one single specific ligand for capture, for a specificity at least comparable to that obtained via a conventional ELISA method using at least two specific antibodies directed against two different epitopes (one capture antibody and one detection antibody), and for a sensitivity close to that obtained via an ELISA method.

The ligand specific to the NS1 protein is chosen from the antibodies, antibody fragments and affinity proteins with competitive properties (Nanofitins™). Preferably, the ligand is an antibody as defined in the "Definitions" paragraph, in particular a monoclonal antibody or a polyclonal antibody highly purified by affinity to NS1 protein. For example, the ligand is a monoclonal antibody specific to the monomeric form, the dimeric form and the hexameric form of NS1 protein.

The ligand is specific to at least one serotype of dengue virus, in particular to two virus serotypes.

In particular the ligand is immobilised on a support such as: a well strip, a plate, a ball, a chip, or chromatographic phase.

DEFINITIONS

Blood sample means whole blood, serum or plasma.

The ligand is preferably an antibody, for instance a monoclonal antibody or a polyclonal antibody highly purified by affinity to NS1 protein, or an affinity protein with competitive properties (Nanofitin™).

The polyclonal antibodies may be obtained by immunising an animal with the appropriate immunogen, followed by recovery of the sought antibodies in purified form, by sampling serum from said animal, and separating said antibodies from the other serum constituents, in particular by affinity chromatography on a column on which is fixed an antigen specifically recognised by the antibodies.

The monoclonal antibodies may be obtained via the hybridoma technique, the general principle of which is reiterated below.

Firstly an animal, generally a mouse, is immunised with the appropriate immunogen, so that its B lymphocytes are then able to produce antibodies against this antigen. These antibody-producing lymphocytes are then fused with "immortal" myeloma cells (murine cells in this example) to generate hybridomas. From the heterogeneous mixture of the cells obtained in this way, we then select the cells capable of producing a particular antibody and multiplying indefinitely. Each hybridoma is multiplied in clone form, each leading to the production of a monoclonal antibody whose recognition properties with respect to the protein will be able to be tested for example by ELISA, immunotransfer (Western blot) in one or two dimensions, by immunofluorescence, or using a biosensor. The monoclonal antibodies thus selected are then purified, in particular by means of the affinity chromatography technique described above.

The monoclonal antibodies may also be recombinant antibodies obtained via genetic engineering, by techniques well known to the person skilled in the art.

Nanofitins (commercial name) are small proteins which, like antibodies, are capable of binding to a biological target, thereby making it possible to detect it, capture it or simply target it within an organism.

FIGURES

FIG. 1 illustrates the amino acids of the amino acid sequence (SEQ ID NO: 1) recognised by the antibodies 12H9G9, 13E1B3, 10G3G13 and 9C9A9. The synthetic NS1 gene is illustrated with its signal peptide (signal peptide of the tissue plasminogen activator—white rectangle) and its polyhistidine tail (black rectangle) necessary for the excretion and purification, respectively, of NS1. The amino acids identified by epitope mapping are identified under the specific sequence (SEC) ID NO: 1) numbered from 1 to 20 (antibodies 12H9G9, 13E1B3, 10G3G13 and 9C9A9). The potential N-glycosylation sites are identified by "V".

FIG. 2 illustrates the detection kinetics of NS1 via SELDI-TOF MS, with antibody 13E1B3 on Vero cells in culture infected by dengue virus serotype 3. The results are presented separately for the culture supernatant and for the cell lysate. FIG. 2A illustrates the results obtained on the culture supernatant, FIG. 2B represents the results obtained on the cell lysate and FIG. 2C illustrates the results obtained with the controls. FIGS. 2A and 2B illustrate the results of the measurements taken respectively at 90 minutes (a); 6 hours (b), 12 hours (c), 24 hours (d), 48 hours (e); 5 days after infection (f), 7 days after infection (g); virus-free control, 7 days after infection. The value associated with the peaks corresponds to the mass over the charge (m/z) after calibration with an internal standard. FIG. 2C illustrates the results of the measurements obtained on additional controls: (a) recombinant NS1 protein (50 ng), (b) culture supernatant of Vero cells infected by serotype-3 dengue virus (7 days after infection), (c) culture supernatant of uninfected Vero cells, (d) lysate of Vero cells infected by serotype-3 dengue virus (7 days after infection), (e) lysate of uninfected Vero cells and (f) culture medium. The value associated with the peaks corresponds to the mass over the charge (m/z) after calibration with an internal standard. FIG. 2D illustrates the results obtained by a sandwich ELISA process. The histograms illustrate the NS1 capture ELISAs performed on the Vero cell lysates (in white) and the culture supernatants (in black) of these same cells, sampled respectively at 90 minutes, 6, 12, 24 and 48 hours, and 5 and 7 days after infection. The values correspond to the optical density (OD) read at 450 nm (average of 2 wells for 2 independent experiments).

FIG. 3 illustrates the detection of NS1 protein via SELDI-TOF MS on plasmas (serotype 3) sampled at different times after the appearance of symptoms; a) culture supernatant of Vero cells infected by serotype-3 dengue virus (2 days post-infection); b) lysate of Vero cells infected by serotype-3 dengue virus (2 days post-infection); c) culture supernatant of uninfected Vero cells; d) lysate of uninfected Vero cells; e) recombinant NS1 protein (50 ng); f) healthy plasma; (g to j) serial samples of plasmas infected by dengue at 2, 3, 4, and 5 days after appearance of the symptoms (p2 to p5). The value associated with the peaks corresponds to the mass over the charge (m/z) after calibration with an internal standard. The histograms illustrate NS1 capture ELISAs performed on the same samples. The values correspond to the optical density read at 450 nm (average of 2 wells for 2 independent experiments).

EXAMPLES

Example 1

Expression And Purification Of A Recombinant Ns1 Protein

The NS1 gene of dengue virus was obtained by reconstituting via overlapping oligonucleotides a synthetic gene for the NS1 protein, taking into account the amino acids present on serotypes 3 and 1 (http://www.ncbi.nlm.nih.gov/genomes/VirusVariation/). The codons were optimised for expression in eukaryotic expression systems. A leader peptide corresponding to the leader peptide of the tissue plasminogen activator was added at the 5' of the gene in order to enable excretion of the synthesised protein[8]. A polyhistidine tail was added at 3', in order to facilitate purification of the protein synthesised using a metal-chelate affinity method. Restriction sites Xho1and Xba1 were also added at the 5' and 3' of the gene respectively. The gene reconstituted in this way was inserted at the sites Xho1-Xba1 of a pCI eukaryotic expression plasmid (Promega-Biotech), governed by a CytoMegaloVirus "early gene" promoter. The NS1 protein is expressed by means of a transient expression technique in eukaryotic cell system 293T (ATCCIDCRL-11268): 293T cells at 70% confluency are contacted with the recombinant plasmid pCI-NS1 in the presence of a transfectant (Lipofectamine 2000, Invitrogen) in accordance with the manufacturer's instructions. Seventy-two hours after transfection, the culture supernatant is recovered at low speed to eliminate the cell debris (1500 g/5 minutes). The preclarified supernatant is then purified. It is contacted overnight at 6° C., under agitation, with a NiNTA resin (Qiagen). The next day, the resin is washed, and then the NS1 protein is eluted in the presence of saline buffer containing 250 μM imidazole, in accordance with the recommendations of *The Quiaexpressionist* (*A handbook for high level expression and purification of his-tagged protein*, fifth edition Qiagen). The imidazole is then eliminated by overnight dialysis against Tris-Buffered Saline pH=7.4 (TBS) in a dialysis cassette of porosity 3500 MWCO (Slide-A-Lyzer, Thermo-Scientific). The dialysed protein may be concentrated by passing over an Ultrafree pod (Millipore). The protein obtained is more than 90% pure. The size estimated via Western blotting, developed with an anti-polyhistidine antibody (PentaHis antibody, Qiagen) after migration on a 10% polyacrylamide gel under denaturing conditions, is approximately 45,000 Daltons, i.e. the size expected for the monomeric protein. Hydrolysis of the N-glycans by PNGaseF (New England Biolabs), followed by electrophoresis on 10% polyacrylamide gel under denaturing conditions confirms, by means of a fall in apparent molecular mass, that the protein obtained is glycosylated. The protein is quantified by micro-BCA (Thermo-Scientific) .

Example 2

Immunisations of Mice and Rabbits and Obtention of Antibodies

Immunisation of mice: the mice immunisation protocol consisted in 5 injections of female 5 Balb/C mice with 50 micrograms of recombinant NS1 protein purified in accordance with example 1 in the presence of Freund's complete adjuvant (first injection) and then incomplete adjuvant, subcutaneously. The interval between each injection is 3 to 4 weeks. At the end of the immunisation protocol, the mice spleen cells are fused with a murine myeloma and cultured until the appearance of clones according to the standard protocol[9]. The hybridomas secreting anti-NS1 antibodies are selected by ELISA: the recombinant NS1 protein, obtained in accordance with example 1, is fixed by adsorption on a 96-well plate at a concentration of 1 µg/mL in Tris-maleate buffer pH=6.2 for one night at 6° C. After 3 washes with 0.1% TBS-Tween, the protein is incubated with the supernatants of the various hybridomas diluted to ½ in 0.1% TBS-Tween-0.1%-Gelatine (TBS-TG) for 1 hour at 37° C. After 3 more washes, a mouse anti-IgG conjugate labelled with horseradish peroxidase diluted in TBS-TG is added and incubated for 45 minutes at 37° C. before the final washes, and then developed using the 1-step Turbo-TMB kit (Thermo-Scientific). A supernatant of non-transfected 293T cells serves as a non-specific signal control. The immunoglobulins of the positive clones are purified by immuno-affinity on protein A sepharose 4FF (GE Healthcare) in accordance with the conventional protocol. Seven monoclonal antibodies were finally selected based on this protocol: 10E2H2, 10G3G13, 13E1B3, 12D2D6, 9C9A9, 12H9G9 and 6H10B9.

Immunisation of rabbits: The protocol consisted of injecting into 3 female New Zealand White rabbits five 200 µg doses of recombinant NS1 protein each. The NS1 protein was obtained as described in example 1. The first three injections were intradermal, and the following two subcutaneous. Freund's complete adjuvant (first injection) and then incomplete adjuvant was added to the protein. A period of 2 weeks was kept between each injection. The rabbits are finally bled 82 days after the first injection, and 60 mL of serum are recovered. The presence of the specific antibodies is checked in accordance with the ELISA described in example 2 (mouse immunisation). The rabbit serums samples taken before immunisation serve as a specificity control. G immunoglobulins are purified on a protein A Sepharose column. The titre of these purified antibodies was estimated via ELISA by means of serial dilution of the antibody on the recombinant NS1 protein coated at the well bottom of a 96-well plate, and after development by a peroxidase-coupled anti-rabbit antibody diluted to 1/5000 using the 1-step Turbo-TMB kit (Thermo-Scientific). The titre, which corresponds to the strongest dilution for which the optical density is three times greater than the background noise obtained with the serums of pre-immune rabbits, is estimated at $10^5$.

Example 3

Characterisation of Monoclonal and Polyclonal Antibodies

Materials and Methods

The antibodies were characterised by various approaches: (i) Western blotting and ELISA on the recombinant NS1 protein or on material infected by dengue virus; (ii) epitope mapping (Spotscan and Phage Display).

(i) For Western blotting, a recombinant NS1 protein, denatured and reduced by the presence of SDS and β-Mercapto-Ethanol in the charge buffer, was used at a final total protein concentration of 0.1 mg/ml. The deposit volume is 20 µl per well, on a NuPAGE Novex 4-12% Bis-Tris gel, MOPS migration buffer (InVitrogen). After migration (at 200 V, for 1 hour) and transfer onto PVDF membrane (at 400 mA, for 45 mins), the transfer quality was assessed by amidoblack coloration. The membranes are saturated by 5% skimmed milk (Régilait) in a TNT solution (15 mM Tris, 0.14M NaCl, 0.5% Tween 20 pH 8) at ambient temperature for 1 hour. After saturation, the membranes are incubated for 1 hour with the various antibodies to be tested diluted to 5 µg/ml in the saturation solution. After rinsing in TNT, the membranes are incubated for 1 hour at ambient temperature with an anti-mouse-phosphatase conjugate diluted to 1:5000 (Jackson Immunoresearch) in the saturation solution. After rinsing, the development is performed with the 1-STEP NBT/BCIP kit (Thermo-scientific) according to the recommended usage data. NS1 could also be detected via a sandwich immunoassay. To do so, the 96-well plates (Nunc) were coated with monoclonal anti-NS1 antibodies to be tested via capture at 2 µg per well. After 3 washes in 0.5% TBS-Tween 20 (TBS-T), the plates are saturated by 10% skimmed milk (Régilait) diluted in TBS-T, for 1 h at 37° C. 3 more washes in TBS-T are performed, and 100 µL of sample to be tested is deposited onto the plates, possibly diluted in TBS-T 1% BSA, and then incubated for 2 h at 37° C. After 3 TBS-T washes, the rabbit anti-NS1 polyclonal antibody (described in example 2) diluted to 1/2000th is added, and incubation is performed for 2 h at 37° C. 3 more washes are performed in TBS-T, before adding the conjugate coupled with horseradish peroxidase (Jackson Immunoresearch) diluted to 1/5000 in TBS-T 3% BSA, at 100 µl/well. After 1 h of incubation at 37° C. and 3 washes in TBS-T, the 1-step Turbo-TMB substrate (Thermo-Scientific) is added, at 100 µl/well. After 20 mins, when the coloration has developed, the reaction is stopped by 1N sulphuric acid, and the absorbance at 450 nm is measured. The results were obtained in the form of gross values after subtracting the background noise.

(ii) The Spotscan technique, adapted as per Frank and Döring[10], makes it possible to simultaneously synthesise a large number of peptides fixed on cellulose membrane. These peptides reproduce the sequence of the target antigen in the form of peptides of 8 to 12 amino acids, overlapping by 1 to 4 residues. These peptides are then contacted with the antibody to be investigated in a Blot-type colorimetric test, and identification of the immunoreactive peptides makes it possible to deduce the minimal sequence of the antibody epitope, and to locate it precisely on the antigen.

The synthesis is performed on a cellulose membrane uniformly carrying polyethylene glycol (PEG) arms 8 to 10 units long, with a free $NH_2$ function at the end of the chain. It runs from the C-terminus end to the N-terminus end of the peptides. The amino acids have their amino function protected by an Fmoc group (9-fluorenylmethoxycarbonyl), and their side chains, which can react during synthesis, are also protected by trityl, t-butyl or t-butyl-ether groups. The amino acid stock solutions are prepared to a concentration of 0.33 M in NMP (N-methyl-pyrrolidone) containing 0.5 M of HOBt (hydroxybenzotriazole). The amino acids are deposited using the robot ASP 222 (Abimed, Langenfeld, Germany), controlled by means of the AutoSpot XL software. Use of this robot makes it possible to simultaneously process up to 4 membranes of 96 spots, i.e. 384 peptides.

For one amino acid coupling cycle, the robot deposits 0.7 µl of the amino acid solution activated extemporaneously (a volume of 1.1M diisopropyl-carbodiimide solution diluted in NMP for 3 volumes of amino acid stock solution) on the membranes. This deposit is repeated a second time, and then the membranes are rinsed in DMF (N,N-dimethylformamide). The $NH_2$ groups that have not reacted are then acetylated by 4 to 6 ten-minute incubations in a 10% solution of acetic anhydride in DMF, in order to prevent the appearance of abortive or truncated peptides. After three 2-minute washes in DMF, the Fmoc groups protecting the amine function of the amino acids are cleaved by a 5-minute incubation in a 20% solution of piperidine in DMF. After 4 washes in DMF, the spots were coloured using a 1% bromophenol blue solution in DMF, and then the membrane is rinsed 3 times in methanol and dried in free air before the next coupling cycle.

This protocol is repeated for the addition of each new amino acid. After the coupling of the last amino acid, the peptides were acetylated in order to block all the free $NH_2$ groups, thus preventing the addition of another amino acid. Then the side chains of all the peptides are deprotected by the incubation of the membranes in a trifluoroacetic acid/dichloromethane/triisobutylsilane bath (5:5:0.3) for 1 hour. The membranes are then rinsed 4 times in dichloromethane, 3 times in DMF and 3 times in methanol before being dried in free air and conserved at −20° C. until immuno-development.

To immuno-develop the spots with a monoclonal antibody, the membranes are firstly rinsed in methanol, and then washed in TBS (50 mM Tris-HCl pH 8.0, 140 mM NaCl, 3 mM KCl) before being incubated overnight at ambient temperature in the saturation solution (casein based 10× concentrated solution (Western Blocking reagent, Roche) diluted in 0.05% TBS-Tween 20 (TBS-T) and containing 5% saccharose). After a 10-minute wash in TBS-T, the membranes are incubated for 1 hour 30 minutes at 37° C. with the monoclonal antibody diluted to 20 µg/ml in the saturation solution. The membranes are then washed 3 times in TBS-T, and are then incubated with the anti-mouse conjugate coupled with alkaline phosphatase (Jackson Immunoresearch), diluted to 1/2000$^{th}$ in saturation solution. After two 10-minute washes in TBS-T, and then 2 washes in CBS (10 mM citric acid pH 7, 140 mM NaCl, 3 mM KCl), the developer, prepared extemporaneously (5-bromo, 4-chloro, 3-indoyl, 600 µM phosphate, 720 µM thiazolyl blue tetrazolium bromide, and 5 mM $MgCl_2$ in CBS), is contacted with the membrane for 30 to 45 minutes in the dark. The immunoreactive peptides appear blue-violet. After 3 rinses in distilled water, the membranes are scanned and then conserved in water until regeneration.

Regeneration makes it possible to eliminate the antibodies and the conjugates fixed onto the peptides, thereby making it possible to perform a new immunoreactivity test with another antibody. The membranes undergo a series of 10-minute washes each: 1 wash in distilled water, 6 washes in DMF, 3 washes in regeneration buffer A (8 M urea, 35 mM SDS (sodium dodecyl sulfate), 0.1% β-mercaptoethanol), 3 washes in regeneration buffer B (distilled water/ethanol/acetic acid 4:5:1), and then 2 washes in methanol. The membranes are then dried in free air before being stored at −20° C.

The epitopes were characterised by screening banks of peptides carried by phages using the commercial kit PhD12 Phage Display Peptide Library Kit (Cat. No. E#8110S) from New England Biolabs, by following the instructions provided with the kit, version 2.7 of the protocol dating from November 2007.

Results:

TABLE 1

| Developing antibody | Recognised forms of recombinant NS1 |
| --- | --- |
| Anti-tag His (Qiagen) | Monomer + Dimer |
| Mab 10E2H2 | Dimer |
| Mab 10G3G12 | Dimer |
| Mab 13E1B3 | Monomer + Dimer |
| Mab 12D2D6 | Dimer |
| Mab 9C9A9 | Dimer |
| Mab 12H9G9 | Monomer + Dimer |
| Mab 6H10B9 | Monomer + Dimer |
| Polyclonal | Monomer + Dimer |

Mab: monoclonal antibody

Table 1 summarises the monomeric/oligomeric forms recognised by the monoclonal antibodies and polyclonal antibody via Western blotting. All the antibodies detect the dimeric form, but the monomeric form is only detected by the monoclonal antibodies 13E1B3, 12H9G9, 6H10B9 and the rabbit polyclonal. The anti-histidine tag antibody recognises the monomeric and dimeric forms. The monomeric form is present because the samples were denatured beforehand. The hexameric form is never recognised, as it is highly instable[5].

TABLE 2

| | Recomb. NS1 | Vero cells infected by DV | |
| --- | --- | --- | --- |
| | | lysates | supernatants |
| 10E2H2 | ++ | DV1-DV2-DV3 | X |
| 10G3G13 | + | DV1-DV2-DV3 | DV3 |
| 13E1B3 | +++ | DV1-DV3 | DV1-DV3 |
| 12D2D6 | + | DV1-DV2-DV3 | X |
| 9C9A9 | ++ | DV1-DV2-DV3 | DV3 |
| 12H9G9 | +++ | DV1-DV3 | DV1-DV3 |
| 6H10B9 | + | DV1-DV2-DV3 | X |
| PA | +++ | NA | NA |
| Platelia ™ | +++ | DV1-DV2-DV3-DV4 | DV1-DV2-DV3-DV4 |

Table 2 recaps the various ELISAs conducted on the recombinant NS1 or on the material coming from Vero cells infected with one of the four dengue virus serotypes (DV1, DV2, DV3 or DV4). The polyclonal antibody (PA) obtained after immunisation of rabbits by NS1 protein, as well as the Platelia kit marketed by BioRad (Platelia™), were also tested by way of comparison. DVx (where x=1, 2, 3, 4) indicates that the signal is considered to be positive for serotype x with an optical density at 450 nm greater than 0.1. The signal intensity is considered to be slight (+) when its optical density is between 0.1 and 0.4 at 450 nm; it is considered to be medium (++) between optical density 0.4 and 0.9, and high (+++) for an optical density reading of greater than 0.9. The best signals obtained on the recombinant protein were obtained with monoclonal antibodies 13E1B3 and 12H9G9, and the rabbit polyclonal antibody. Only the monoclonal antibodies 10G3G13, 13E1B3, 9C9A9 and 12H9G9 can detect the mature NS1, secreted in the culture supernatant by Vero cells infected by dengue virus. Specificity is restricted to serotypes 1 and 3 for monoclonals 13E1B3 and 12H9G9. It is restricted to serotype 3 for 10G3G13 and 9C9A9.

Epitope Mapping:

Epitope mapping gave usable results only for monoclonal antibodies 13E1B3, 12H9G9, 10G3G12 and 9C9A9. All the antibodies except for 12H9G9 (which was mapped using the Phage display technique) were mapped using the Spotscan technique. The results obtained are illustrated by FIG. 1. For 13E1B3, 12H9G9, the epitopes are non-continuous. 10G3Gl2 and 9C9A9 have the same linear epitope. All the epitopes characterised are concentrated on a peptide of 20 amino acids located in the C-terminus half of the NS1 protein. This peptide corresponds to a fairly well conserved sequence. Some amino acids of this peptide are nonetheless serotype-dependent, especially those situated downstream of glycine 13 (see numbering in FIG. 1), and may explain the restriction of 13E1B3 and 12H9G9 to recognition of serotypes 1 and 3. Interestingly, this region of NS1 has already been identified as immunodominant for serotype-2 dengue virus[11].

For the SELDI-TOF MS detection experiments, monoclonal antibodies which could recognise at least the monomeric form of the recombinant NS1 protein with in addition a good level of recognition via ELISA were selected. These antibodies also had to recognise the mature forms of the NS1 protein which were secreted in an in vitro infection system of Vero cells by dengue virus. Antibodies 13E1B3 and 12H9G9 meet these criteria. They detect the mature forms of NS1 of serotype-1 and 3 dengue virus. The mature forms correspond to the forms excreted by the cells in the culture supernatant; they lack a signal peptide, are glycosylated and multimeric, i.e. at least dimeric.

Example 4

Capture ELISA and SELDI-TOF Comparison on In Vitro Infected Material

Materials and Methods:
Vero cells (ATCC IDCCL81) cultivated in DMEM, supplemented by 10% foetal calf serum (DMEM-SVF), are infected at the sub-confluency stage (90% confluency). After 90 minutes of contact of the cells with one of the viral strains (DV1, DV2, DV3, DV4; Sanofi-Pasteur) diluted in 1 mL of DMEM without serum to a Multiplicity of Infection (MOI) of 0.1, the inoculum is replaced with 10 mL of DMEM-SVF medium. An aliquot of culture supernatant is harvested at different post-infection incubation times (90 minutes, 6, 12, 24 and 36 hours, 5 and 7 days). The dead cells are eliminated by a centrifugation of 5000 g/5 minutes. The cell lysate is obtained after the same incubation times with the virus. In this case, 1 mL of lysis buffer (TBS-NP401%) is added onto the cell layer, and is left to act for 15 minutes at 4° C. The debris is eliminated by a centrifugation of 10,000 g/5 minutes. The infection is controlled using Platelia™ ELISA (BioRad), which detects the presence of NS1 protein in the culture supernatant.

The capture ELISAs are performed as described in example 3, using the antibodies obtained via mice immunisations for capture (see example 2).

SELDI-TOF MS technology was developed for mass spectrometry analysis of protein mixtures specifically retained by chromatographic surfaces. In this case, the chromatographic surface is coupled with an anti-NS1 antibody selected for its ability to recognise the recombinant NS1 and NS1 synthesised in vitro after infection of Vero cells. The antibodies are coupled on a pre-activated PS20 well strip (epoxy group) by incubation of 0.6 µg of antibody for 1 hour at ambient temperature. The well strips were then saturated for 5 minutes with 0.5% PBS-TritonX100 and washed once with PBS. The samples (50 µl), diluted once with PBS, are deposited onto the saturated well strips and incubated for 2 hours at ambient temperature in a suitable bioprocessor. Finally, they are washed 3 times with 0.05% PBS-TritonX100, and then 2 times with PBS, in order to eliminate the detergent. An extemporaneously produced 0.5% SPA-TFA matrix is then added before reading on the apparatus in accordance with the manufacturer's instructions (Ciphergen Protein Biology System II (commercial name), Biorad). The spectra are calibrated by means of an internal standard (ProteinChip All-in-one standard II (commercial name), Biorad) and are analysed using an appropriate software (ProteinChip Software V3 (commercial name), Biorad). All the samples were analysed twice independently. The consumables associated with this technology are marketed by BioRad. The samples analysed comparatively by the two technologies are as follows:

Lysates and culture supernatants sampled at 90 minutes; 6, 12, 24, 48 hours; 5 and 7 days post-infection;
Recombinant NS1 protein (50 ng) diluted in healthy plasma (i.e. coming from a patient without dengue);
Lysates and culture supernatants of uninfected Vero cells (7 days post-infection);
Culture medium.

For SELDI-TOF, the value associated with the peaks corresponds to the mass over the charge (m/z) after calibration with an internal standard. The NS1 capture ELISAs are illustrated by histograms performed on the same samples. The values correspond to the optical density read at 450 nm (average of 2 wells for 2 independent experiments).

Figure 2:
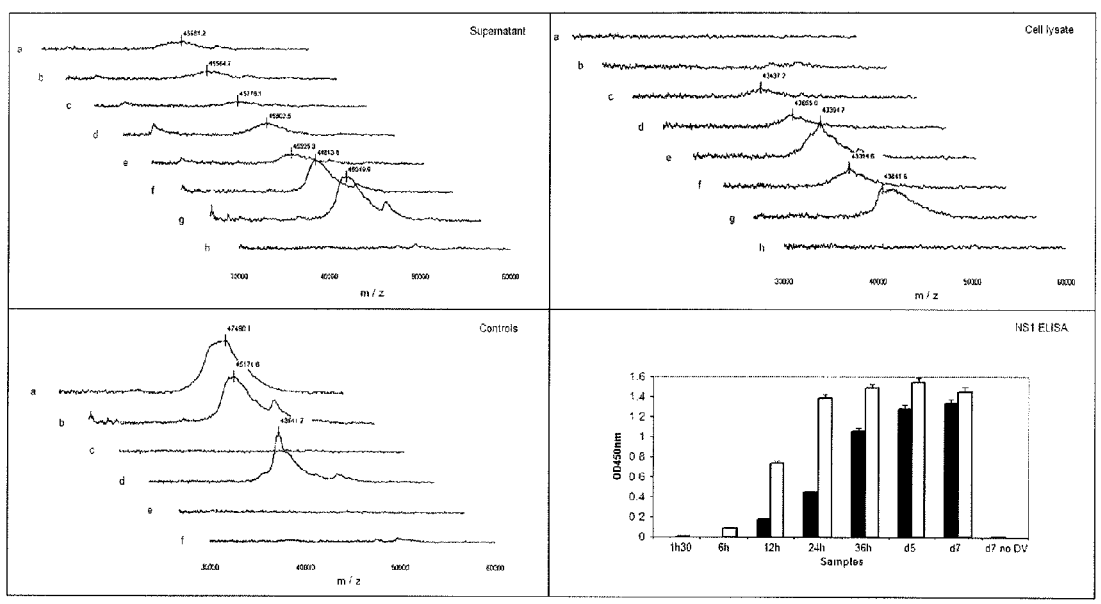

Results:
The results obtained on material infected by the serotype-3 virus with antibody 13E1B3 are presented in FIG. 2. The same experiment, but conducted with antibody 12H9G9, gave comparable results. On the infected cell lysates, 12 hours after infection the appearance of a peak was noted at around 43,500 Daltons (Da), present in subsequent samples. This peak is absent from the uninfected cell lysates. On the culture supernatant, a peak of around 45,500 Da appears unambiguously 24 hours after infection. This peak is absent from the culture supernatants of uninfected cells. However, a slight signal seems to be present 90 minutes and 6 hours after infection: it is probably due to the small quantities of NS1 protein provided by the viral inoculum upon infection, which subsequently disappear through degradation (12 hours after infection). The difference in molecular mass observed between the NS1 proteins in the lysate and supernatant is probably due to the post-translational modifications associated with the protein excretion (glycosylation in the late Golgi, for example). The recombinant NS1 protein is detected at a similar molecular mass. Similar results were obtained with Vero cells infected with serotype-1 dengue virus. No signals are detected on material infected with serotypes 2 or 4, which is consistent with the nature of the immunogen used, which was similar to serotypes 1 and 3. A capture ELISA used on the same samples confirms these results: the NS1 protein is present in the lysates and the supernatants after infection. It is detected in the lysates of the infected cells before being detected in the culture supernatants (6 hours as opposed to 12 hours). As is apparent from FIG. 2, the specificities obtained using an ELISA or a SELDI TOF MS are comparable. However, under the test conditions, using monoclonal antibodies 13E1B3 and 12H9G9 as capture antibodies, serotypes 2 and 4 are not detected via SELDI TOF MS, which indicates that SELDI TOF MS is a serotype-specific method according to the antibody used for capture.

Example 5

ELISA and SELDI-TOF Comparison on Serial Human Samples

Materials and Methods:

The capture ELISA and SELDI-TOF MS techniques developed and described in examples 3 and 5 are used to comparatively evaluate the presence of NS1 in the plasmas of a patient infected by serotype-3 dengue virus (DV3), and sampled 2, 3, 4, 5 days after the appearance of symptoms. These samples come from a retrospective study initially conducted by Louis Malarde Institute, Papeete (Tahiti). This study was reviewed and approved by the local ethics committee. The samples were as follows:

Culture supernatants and lysates of Vero cells infected by serotype-3 dengue virus (2 days post-infection);
Culture supernatants and lysates of uninfected Vero cells;
Recombinant NS1 protein (50 ng) diluted in healthy plasma (i.e. from a patient without dengue);
Healthy plasma (i.e. from a patient without dengue);
Serial plasma specimens (infection with serotype-3 dengue virus) at 2, 3, 4, and 5 days after appearance of the symptoms.

The value associated with the peaks corresponds to the mass over the charge (m/z) after calibration with an internal standard. The histograms illustrate NS1 capture ELISAs performed on the same samples. The values correspond to the optical density read at 450 nm (average of 2 wells for 2 independent experiments).

Figure 3:
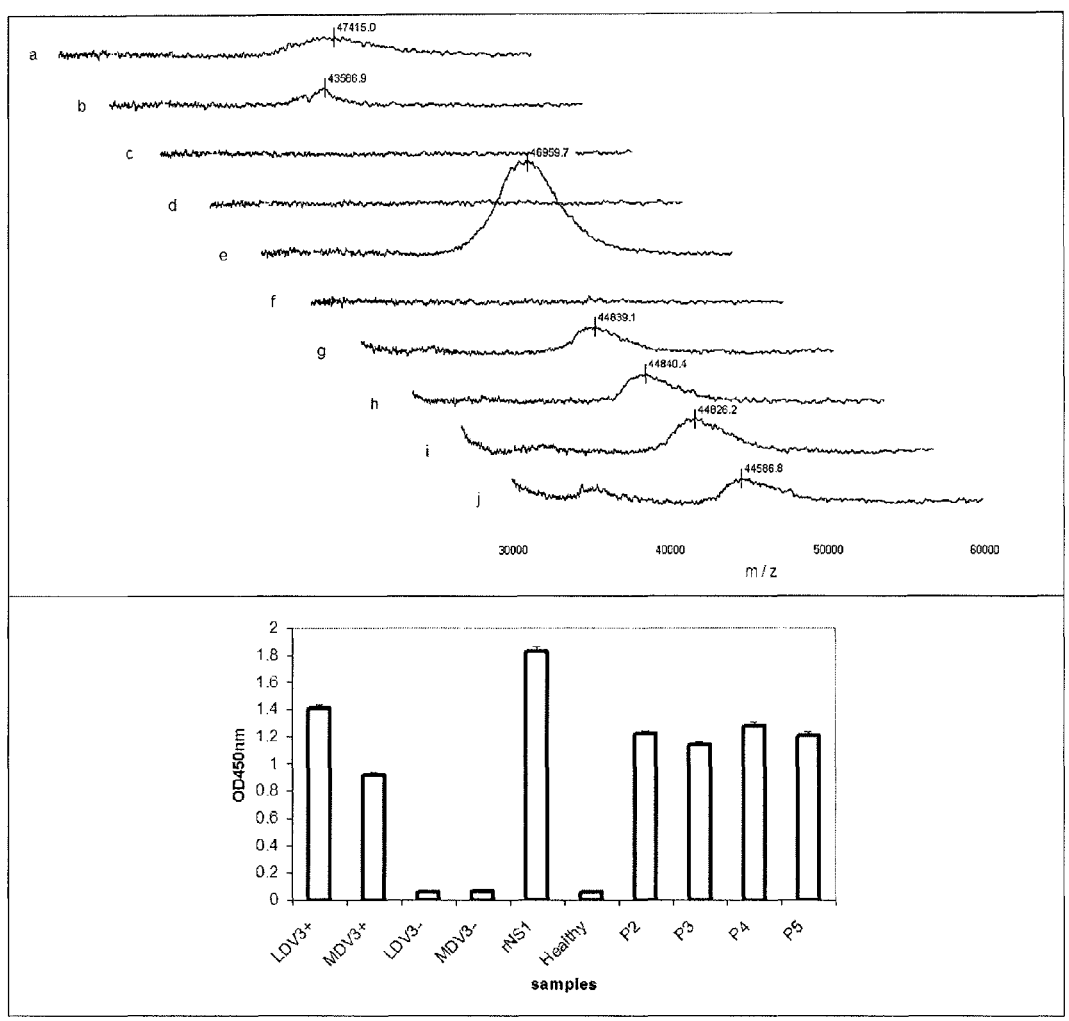

Results:

The results obtained with antibody 13E1B3 are presented in FIG. 3. The same experiment, but conducted with antibody 12H9G9, gives comparable results.

There is a signal on the "serotype-3" plasmas from two days after the appearance of symptoms. This signal has a molecular mass of approximately 45,000 Da, comparable to that obtained with a recombinant NS1 in solution (1 ng/uL) or on samples obtained from in vitro infection of Vero cells. There is no signal on healthy plasmas or on the material uninfected by dengue virus. Similarly, a signal could be detected on two serotype-1 plasmas (4 and 5 days after the appearance of the symptoms), but not on two serotype-2 plasmas (4 days after the appearance of the symptoms). The results obtained via SELDI-TOF MS were confirmed via capture ELISA.

Therefore SELDI-TOF MS enables the detection of NS1 in a complex biological medium, using just one specific monoclonal antibody with good specificity. The sensitivity is close to, although slightly less than, that of a conventional ELISA. The technique also makes it possible to detect small modifications to the protein (glycosylations for example) and to detect, according to the chosen antibody, the various virus serotypes from NS1.

BIBLIOGRAPHIC REFERENCES

1. S B Halstead. The Lancet 2007; 370: 1644-52
2. AS Leong et al. Semin. Diagn. Pathol. 2007; 24(4): 227-236
3. K. Clyde et al. J. Virol. 2006; 23: 11418-11431
4. G. W Smith, J. Gen. Virol, 66, 559-571
5. P. Avirutnan et al., JID 2006; 193: 1078-108 G. W Smith[4] (J. Gen. Virol, 66, 559-571)
6. Flamand et al. J. Virol, 73(7): 6104-6110
7. Hutchens et al. (Adv Exp Med Biol. 1998; 443:23-3
8. Ashock M S et al. Vaccine, 2002
9. G. Köhler and C. Milstein, 1976, Eur J Immunol, 6, 511-519
10. R. Frank and R. Dohring, 1988, Tetrahedron, 44, 6031-6040
11. Vaughan et al., Viral Immunol., 23(3), 259-284

The invention claimed is:

1. A process for detecting an NS1 protein of a dengue virus, comprising:
   contacting a blood sample from an individual with a ligand immobilized on a solid support that is specific for SEQ ID NO: 1 to capture NS1 protein if present in the blood sample; and
   detecting whether the NS1 protein has been captured with mass spectrometry.

2. The process of claim 1, wherein the ligand is selected from the group consisting of antibodies, antibody fragments, and proteins specific for SEQ ID NO: 1.

3. The process of claim 1, wherein the ligand is an antibody or antibody fragment specific for SEQ ID NO: 1.

4. The process of claim 1, wherein the ligand is a monoclonal or polyclonal antibody specific for SEQ ID NO: 1.

5. The process of claim 1, wherein the ligand is a monoclonal antibody that binds an epitope within SEQ ID NO: 1.

6. The process of claim 1, wherein the ligand is specific for more than one dengue virus serotype.

7. The process of claim 1, wherein the solid support is a well strip, a plate, a ball, a chip, or a chromatographic phase.

* * * * *

```
SEQUENCE LISTING

<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: synthetic construct

<400> SEQUENCE: 1

Gly Tyr His Thr Gln Thr Ala Gly Pro Trp His Leu Gly Lys Leu Glu
1               5                   10                  15

Leu Asp Phe Asp
            20
```